(12) United States Patent
Chwalisz et al.

(10) Patent No.: US 6,333,350 B1
(45) Date of Patent: Dec. 25, 2001

(54) USE OF NITRIC OXIDE DONORS AND/OR SUBSTRATES OR NITRIC OXIDE INHIBITORS FOR REGULATING CERVICAL DILATATION AND EXTENSIBILITY

(75) Inventors: Kristof Chwalisz, Berlin (DE); Robert E. Garfield, Friendswood, TX (US)

(73) Assignees: Schering AG, Darmstadt (DE); University of Texas System, Galveston, TX (US)

( * ) Notice: Subject to any disclaimer, the term of this patent is extended or adjusted under 35 U.S.C. 154(b) by 0 days.

(21) Appl. No.: 09/236,085

(22) Filed: Jan. 25, 1999

Related U.S. Application Data

(63) Continuation of application No. 08/913,305, filed as application No. PCT/US96/03540 on Mar. 14, 1996.

(30) Foreign Application Priority Data

Mar. 14, 1995 (EP) .................................. 95250059

(51) Int. Cl.⁷ ................ A61K 31/21; A61K 31/045; A61K 31/195
(52) U.S. Cl. ................ 514/509; 514/727; 514/565
(58) Field of Search .................... 514/509, 727, 514/565

(56) References Cited

U.S. PATENT DOCUMENTS 5,508,045  4/1996  Harrison et al. .................... 424/608

FOREIGN PATENT DOCUMENTS

| WO 95/13802 | 11/1994 | (WO) . |
| WO 95/23345 | 2/1995  | (WO) . |
| WO 96/28145 | 3/1996  | (WO) . |

OTHER PUBLICATIONS

International Search Report (dated Mar. 14, 1995).

M. Shiotani et al., *ACTA Histochem. Cytochem*, vol. 26, No. 1, pp. 57–64 (1993).

C. Lees et al., *The Lancet*, vol. 343, pp. 1325–1326 (1994).

A. J. Thomson et al., *The British Journal of Obstetrics and Gynecology*, vol. 104, pp. 1054–1057 (1997).

*Primary Examiner*—Theodore J. Criares
*Assistant Examiner*—Jennifer Kim
(74) *Attorney, Agent, or Firm*—Millen, White, Zelano & Branigan, P.C.

(57) ABSTRACT

The invention describes the regulation of cervical dilatation and extensibility by the use of nitric oxide donors and/or substrates or nitric oxide inhibitors. There can be used either (a) at least one nitric oxide donor and/or substrate for manufacture of a medicament to be administered locally intracervically or intravaginally for induction of cervical ripening or (b) at least one nitric oxide inhibitor for manufacture of a medicament to be administered locally intracervically or intravaginally for treatment of cercvical insufficiency or preterm labor.

31 Claims, 9 Drawing Sheets

USE OF NITRIC OXIDE DONORS AND/OR SUBSTRATES OR NITRIC OXIDE INHIBITORS FOR REGULATING CERVICAL DILATATION AND EXTENSIBILITY

This is a continuation of application Ser. No. 08/913,305 filed Nov. 19, 1997; which is based on PCT application Ser. No. PCT/US96/03540, filed Mar. 14, 1996.

BACKGROUND OF THE INVENTION

1. Field of the Invention

The present invention relates to the regulation of cervical dilatation and extensibility by the use of nitric oxide donors and/or substrates or nitric oxide inhibitors.

2. Description of the Related Art

Parturition (expulsion of the fetus from the uterus), requires both contractions of the myometrium, the smooth muscle of the uterus, and a softening of the connective tissue of the cervix, so that it will stretch and dilate sufficiently to allow the fetus to be expelled. This softening is known as "ripening".

The current preferred method of cervical ripening is by the use of prostaglandin $B_2$. This is used as a vaginal gel or tablet or as a gel placed in the cervix. One worry about the use of prostaglandin $E_2$ is that there is a possibility of hyperstimulation of the uterus, leading to excessively strong myometrial contractions before the cervix is ripened and therefore before a comfortable or safe birth is possible.

The ideal preparation would soften and efface the cervix without causing myometrial contractions. This would allow the subsequent contractions (induceable if necessary with a small dose of prostaglandin) to deliver the baby with a minimum of resistance. There is good evidence from animal experiments that the antiprogestins such as RU486 would meet these requirements, but the problem with this drug is that it has associated antiglucocorticoid activity which might be detrimental to the fetus.

One of the most exciting recent advances in biology and medicine is the discovery that nitric oxide is produced by endothelial cells and that it is involved in the regulation of vascular tone, platelet aggregation, neurotransmission and immune activation (Furchgott and Zawadzki, 1980; Moncada, Palmer and Higgs, 1991; Ignarro, 1991). Nitric oxide is an important mediator of relaxation of the muscular smooth muscle (Montada, Palmer and Higgs, 1991) and was formerly known as EDRF (endothelin-derived relaxing factor) (Furchgott und Zawadzki, 1980; Moncada, Palmer and Higgs, 1991).

Nitric oxide is synthesized by the oxidative deamination of a guanidino nitrogen of L-arginine by at least different isoforms of a flavin-containing enzyme, nitric oxide synthase (Montada, Palmer and Higgs, 1991).

Nitric oxide can also be generated by application of various nitric oxide donors such as sodium nitroprusside, nitroglycerin, glyceryl trinitrate, SIN-1, isosorbid mononitrate, isosorbid di nitrate, etc.

Synthesis of nitric oxide has been shown to be competitively inhibited by analogies of L-arginine; NG-nitro-Larginine methyl ester (L-NAME), NG-monoethyl-L-arginine (LMMA), N-iminoethyl-L-amithine (L-NIO), L-monomethyl-Larginine (L-NNMA), L-NG-methylarginine (LNMA), Nw-nitro-L-arginine (L-NA) and Aminaguanidine. Treatment of nonpregnant guinea pigs with L-NAME results in increased uterine contractility. Thus, inhibition of nitric oxide synthase-stimulated uterine contractility indicates that the tonic release of nitric oxide maintains the uterus in a quiescent state. Similarly, treatment of pregnant guinea pigs with L-NAME induced preterm labor. On the other hand, treatment of rat uterine strips in vitro with L-arginine inhibited contractions. These studies show that nitric oxide production by the uterus inhibits uterine contractility and a blockade of this synthesis results in increased muscle contractility both in pregnant and non-pregnant animals. Thus, nitric oxide substrates or donors are useful therapeutically to prevent uterine contractility and nitric oxide inhibitors are effective in stimulating uterine contractions.

Based on preliminary studies using rhesus monkees, Jennings et al. (The Journal of Maternal-Fetal Medicine 2:170–175 (1993)) have suggested that nitric oxide may be important in uterine quisence during pregnancy, and exogenous nitric oxide may be useful in controlling preterm labour.

Nitric oxide synthase (NOS) activity was demonstrated in multiple structures within the gravid rat uterus by Natuzzi et al. (Biochem. and Biophys. Res. Commun., 194, No.1, 1–8, (1993)) and they conclude NOS to be present within multiple structures of the gravid rat uterus. Reduction in NOS activity at parturition suggests NO may contribute to the maintenance of uterine contractile quisence during gestation.

Also, morphological studies have already shown the occurence of NOS (NADPH-diaphorase, a histochemical method detecting all NOS isoforms) and NO metabolizing enzymes such as superoxide dismutase in the cervix (Papka et al., Neuroscience Letters 147 (1992); Shiotani et al., Acta Histochem. Cytochem. 26:57–64 (1993)).

It has now been found that L-NAME treatment s.c. in pregnant guinea pigs on days 48–49 p.c. (term day 67+3 days) surprisingly led to a reduction in the cervical extensibility and a reduction in the cervical dilatation.

In pregnant rats, an increased production of nitric oxide (parameter, nitrite and nitrate release in vitro) from the uterine cervix has been found at the time of delivery in comparison with day 18 of pregnancy. In contrast there was a reduction in the uterine (myometrial) NO production in the course of rat pregnancy. The antiprogestins onapristone increased the nitric oxide production in the uterine cervix in pregnant rats still further, but had an inhibitory effect on the NO production in the uterus (myometrium). Treatment with the same dose of onapristone induced cervical ripening in rats.

These findings show that treatment with a nitric oxide inhibitor such as L-NAME inhibits cervical ripening but stimulates uterine contractions in pregnant guinea pigs;

the NO production, which has a relaxing effect on the myometrium, decreases in the pregnant uterus (myometrium) during the course of pregnancy, but it increases in the uterine cervix during normal and antiprogestin-induced parturition in rats;

the divergent effects of a nitric oxide inhibitor such as L-NAME on uterine contractility and uterine cervix are due either to different actions of the NO-system or to the presence of different enzyme isoforms in the myometrium and cervix and the NO-system plays an important role in the control of uterine cervix, the NO production being increased during the ripening process of the cervix.

It is, therefore, concluded that:

(a) a local application of nitric oxide donors and/or substrates can be used to induce cervical ripening or (b) a local application of a nitric oxide-inhibitor can be used to prevent or inhibit cervical ripening, e.g. for the treatment of cervical insufficiency (too early cervical ripening) or preterm labour.

Thus the present invention is directed to the use of nitric oxide donors and/or substrates or nitric oxide inhibitors for manufacture of a medicament for regulating cervical dilatation and/or extensibility.

The present invention involves the use of either (a) at least one nitric oxide donor and/or substrate for manufacture of a medicament to be administered locally (e. g. intracervically or intravaginally) for induction of cervical ripening or (b) at least one nitric oxide inhibitor for manufacture of a medicament to be administered locally (e. g. intracervically or intravaginally) for inhibition of cervical rirening for treatment of cervical insufficiency or preterm labor.

Suitable for the purposes of this invention as (a) nitric oxide donor and/or substrate or (b) nitric oxide inhibitor are all the compounds known to the persons skilled in the art as having the required properties; the compounds mentioned under "Description of related art" are preferred.

The nitric oxide donor and/or substrate (a) can further be used in combination with (i) at least one of an antiprogestin, a prostaglandin and/or a cytokine.

Examples for antiprogestins are onapristone (11β-[4(Dimethylamino)phenyl]-17α-hydroxy-17β-(3-hydroxypropyl)-13α-estra-4,9-diene-3-one), RU 486 (11β-[4-(Dimethylamino)phenyl]-17β-hydroxy-17α-(1-propinyl)estra-4,9-diene-3-one), (Z)-11β-[4-(Dimethylamino)phenyl]-17β-hydroxy-17α-(3-hydroxy-1-propenyl)estr-4-ene-3-one (EP-A 0 404 283), 11β-(4-Acetylphenyl)-17β-hydroxy-17α-(1-propinyl)estra-4,9diene-3-one (EP-A 0 190 759), 4',5'-Dihydro-11β-[4-(dimethylamino)phenyl]-6β-methylspiro[estra-4,9-diene-17β,2'(3'H)-furan]-3-one, 4',5'-Dihydro-11β-[4-(dimethylamino)phenyl]-7β-methylspiro[estra-4,9-diene-17β,2'(3'H)-furan]-3-one 11β-(4-Acetylphenyl)-19,24-dinor-17,23-epoxy-17α-chola-4,9,20-triene-3-one, (E)-11β-[4-[[(Acetyloxy)imino]methyl]phenyl]-17β-methoxy-17α-(methoxymethyl)estra-4,9-diene-3-one (E)-11β-[4-[[[(Ethoxycarbonyl)oxy]imino]methyl]phenyl]-17β-methoxy-17α-(methoxymethyl)estra-4,9-diene-3-one and a lot of other compounds having competitive progesterone antagonistic activity which are well known to the skilled persons.

As prostaglandins suiprostone ($PGE_2$) or gemeprost can be used for instance.

The most prominent representatives for the cytokines are the interleukin-8 or interleukin-1β.

These listings are not to be regarded as exhaustive.

The nitric oxide inhibitor (b) can further be used in combination with (ii) at least one of a progestin and/or a cyclooxygenase inhibitor (e. g. COX-1- and COX-2-inhibitors).

As a progestin, the naturally occuring progesterone is preferred but it is also possible to use one or more of the numerous synthetic progestins known to the artisan for use in oral contraceptives, for example levonorgestrel, cyproterone acetate, gestoden, drospirenone, desogestrel, 3-ketodesogestrel, dienogest etc.

The cyclooxygenase inhibitor can be for example aspirin (COX-1- and COX-2-inhibitor). Further examples of COX-2 inhibitors can be taken from: Robert Aslanian, Nicholas I. Carruthers, James J. Kaminski; Cyclooxygenase 2: A Novel Target for Therapeutic Intervention, Exp. Opin. Invest. Drugs, 1994, 3 (12), 1323–1325, for instance the compounds Sc-58125 (GD Searle), DuP-697, flusolide [6-(2,4-difuorophenoxy)-5-methylsulfonylamino-1-indanone], Sc-57666 (GD Searle), L-745 337 (Merck Frosst), NS-398 (Monsanto).

In its first aspect (a) the invention provides the use of these compounds of the invention in connection with birth or abortion. In this situation of pregnancy the cervix is pretreated. The hormones during pregnancy alter the cervix which is then inclined to respond effectively to other stimulants.

Further the invention provides the use of the compounds under (a) of the invention in connection with surgical procedure and diagnostic procedure. Therefore, the compounds under (a) of the invention can, optionally in combination with the compounds mentioned under (i), be used for manufacture of medicaments for the following indications:

(A) induction of labour at term (time of ordinary birth, can be combined with sequential treatment with oxytocin or similar agents), (B) induction of labour in connection with a pathological pregnancy (e.g. fetal malformation); (preferred second trimester abortion), (C) induction of labour in connection with intrauterine fetal death, (D) induction of abortion (preferred first trimester abortion), (E) induction of preterm labour, (F) management of prolonged labour due to cervical dystocia, (G) induction of cervical ripening of a non-pregnant female or pregnant female to assist for surgical or diagnostic procedure, and (H) induction of cervical ripening for female to be treated by in vitro fertilisation.

In its second aspect (b) the invention provides the use of these compounds of the invention in indications which require the prevention of too early cervical ripening or where the cervix has to be kept rigid. Therefore the compounds under (b) of this invention can, optionally in combination with the compounds mentioned under (ii), be used for manufacture of medicaments for the following indications:

(I) treatment of cervical insufficiency (cervical incompetence) and (K) treatment of threatening preterm labour.

In principle the compound can be used for human and non-human females. Human beings arc the preferred group for this treatment.

The nitric oxide donor and/or substrate (a) or the nitric oxide inhibitor (b) can be administered in any way in which, directly or indirectly, it will reach the cervix. Thus, it is conveniently applied intravaginally or directly to the cervix, e.g. typically as a gel or cream. It can also be injected into the cervical tissue or by a blunt needle into the cervical channel. It can also be applied extra-amniotically, i.e. between the uterine wall and the amniotic sac, using a catheter.

The preferred formulation is a gel or cream, but it can be applied as softenable capsules, liposomes or in a slow release formulation, or as an aqueous solution, e.g. a saline or protein-containing solution. The formulation can be achieved by methods known to the persons of ordinary skill in the art.

If a combined use of the compounds as mentioned above under (a) and (i) is intended the antiprogestin can be formulated for systemic or topical administration. The prostaglandin as well as the cytokine will be preferably formulated for local use.

If a combined use of the compounds as mentioned above under (b) and (ii) is intended, the compounds under (ii) can be formulated for local or systemic application.

The formulations of the compounds under (i) and (ii) can be achieved in ways known to those skilled in the art.

The compounds as under (a) of the invention exhibit pharmacological activity in induction of cervical ripening and may, therefore, be useful as a pharmaceutical agents.

The compounds as under (b) of the invention exhibit pharmacological activity in preventing cervical ripening and may, therefore, be useful as a pharmaceutical agents.

The measurement of the cervix ripening is described in Example 1.

Sodium nitroprusside and other nitric oxide donors show an effect on the cervical ripening at concentrations of from about 0.03 mM–100 mM (1.8 µg–6 mg/application) when locally administered to pregnant female guinea-pigs. For these indications mentioned before under (A) to (F) the appropriate dosage will, of course, vary depending upon, for example, the compounds of the invention employed, the host, the mode of administration and the nature and severity of the condition being treated. However, in general, satisfactory results in animals are indicated to be obtained at a concentration from about 0.03–100 mM in the local formulation, preferred at a concentration of about 10 mM.

The compounds of the invention can be administered 6 to 48 hours before the final ripening of the cervix. The ripening can be proceeded by induction of labour with an oxytocic compound. The compounds can be administered in one or more dosages administered in a series with a distance of some hours or one day. The compounds of the invention may be administered by any conventional route, in particular in form of gel, ointment or local injection (at a concentration of about 0.03 to 100 mM).

Sodium nitroprusside and other nitric oxide donors show an effect on the cervical ripening at concentrations of from about 0.03 mM–100 mM (1.8 µg–6 mmg/application) when administered to female guinea-pigs which are not pregnant. For these indications mentioned before under (G) to (H) the appropriate dosage will, of course, vary depending upon, for example, the compounds of the invention employed, the host, the mode of administration and the nature and severity of the condition being treated. However, in general, satisfactory results in animals are indicated to be obtained at a dosage from about 0.03 mM–100 mM (1.8 µg–6 mmg/application), preferred at a concentration of about 10 mM. These compounds of the invention can be administered 24 or 48 hours before the final ripening of the cervix. The compounds can be administered in one or more dosages administered in a series with a distance of some hours or one day. The compound of the invention may be administered by any conventional route, in particular in form of gel, ointment or local injection.

Examples of human dosage ranges of typical NO-substrates and NO-donors are:

| L-Arginine | 500 mg–10 g/day |
| Sodium nitroprusside | range 500–2000 µg/kg/day |
| Nitroglycerine | 0.5–10 mg/day |
| Isosorbid mononitrate | 10–100 mg/day |
| Isosorbid dinitrate | 10–100 mg/day. |

Other NO-donors or NO-substrates are used in bioequivalent amounts.

Examples of dosage ranges of typical NO-inhibitors are:

| L-NAME | 1 to 50 mg/kg/day |
| L-NIO | 1 to 50 mg/kg/day |
| L-NA | 1 to 50 mg/kg/day |
| L-MMA | 1 to 50 mg/kg/day |
| L-NG | 1 to 50 mg/kg/day |
| L-NMA | 1 to 50 mg/kg/day. |
| Aminoguanidine | 0.1 to 100 mg/kg/day. |

Other NO-inhibitors are used in bioequivalent amounts.

Dosage range for RU 486: 25–600 mg/day per os.

Other antiprogestins are used in biologically equivalent amounts.

Dosage range for suiprostone: 100–1000 µg/day i.m. or i.v.

Other prostaglandins such as $PGE_2$ are used in bioequivalent amounts.

The prostaglandins can also be used locally intracervically in gel, intravaginally in gel or as tablets.

Dosage range for COX-2 inhibitors: 0.1–100 mg/kg/day.

Dosage range for IL-8: 100 ng–500 µg/day; dosage range for IL-1β: 100 ng–500 µg/day.

Bioequivalent amounts of other compounds than those mentioned above can be determined by the methods as disclosed in the examples as such amounts which lead to comparable effects in the cervix as the specifically disclosed amounts under otherwise analogous conditions.

The results of the invention are supported by the Figures which show the following:

FIGS. 1 (A and B) shows the effect of sodium nitroprusside on cervical ripening in pregnant guinea pigs. Animals are treated as described in Example 1. The upper panel (FIG. 1A) shows the initial dilatation (in mm) during extensibility measurement; the lower panel (FIG. 1B) emonstrates the effect on the extensibility (slope of the regression curve). The data are presented as box plots. The vertical lines represent the range from the lowest to the highest amount. The height of the box, the horizontal line, and asterisk describe the inter quartile range, median, and mean value, respectively.

FIGS. 2 (A and B) shows the effects of L-NAME on the uterine cervix in pregnant guinea pigs. The upper panel (FIG. 2A) shows the initial dilatation (in mm) during extensibility measurement; the lower panel (FIG. 2B) demonstrates the effect on the extensibility (slope of the regression curve [N/mm]). Data are presented as box-plots as described for FIG. 1.

EXAMPLE 1

The Influence of Nitric Oxide on Cervical Ripening in Pregnant Guinea Pigs (a) General Part:

Measurement of the ripening:

Entire cervices are obtained from guinea pigs at day 44 post coitum. The extensibility studies are performed by a modification of the method described in the publication DOWNING, S. J. and SHERWOOD, O. D. (1985) Endocrinology 116: 1215–1220. The isolated cervix is mounted between two hooks inserted through each canal of the cervix. One hook is fixed, the other is moved upwards while force and displacement are measured with a sampling rate of 1 Hz. First each cervix is extended until a force of 50 mN is reached. The associated displacement is recorded and will be called initial dilation. Thus the original inner circumference of the cervix is double the initial dilation.

Afterwards the cervix is extended by moving the hook for 0.1 mm, then the hook is fixed and the cervix allowed to relax for 2 minutes. This is repeated until either the cervix ruptures or at least the yield point has been reached, i.e. the envelope of the load vs. time curve becomes non-linear (see the publication CONRAD, J. T. and UELAND, K (1979) Am J Obstet Gynecol 133: 11–13)

(b) Analysis:

To determine the extensibility of the cervix the force vs. stretch ratio curve is studied. This curve is obtained by taking the maximum force at each extension stage and the associated stretch ratio, which is defined as displacement divided by the initial dilation. The slope of a regression line through the linear portion of this curve is taken to quantify the effect of treatment on cervical extensibility. A decrease in the slope represents an increase in the cervical extensibility (ripening effect).

ps (c) Special Part:

Pregnant guinea pigs which are at day 42 post coitum (n=6 animals per group) were treated intracervically twice-a-day with 200 $\mu L$ gel (3% hydroxycellulose) containing 0.03 mM sodium nitroprusside on day 42 and day 43 (at 9:00 a.m. and 5:00 p.m.). The measurement of cervical extensibility (parameters: slope of the regression line, initial dilatation) was performed on d44 p.c.

The gel is administered by the following method: After introduction of the speculum into vagina, 200 $\mu l$ of cellulose gel with or without SNP is injected through ca. 100 mm long blunt needle into cervical channel. Part of the gel moves along the channel to take place around os internum of the uterine cervix. The gel has the following formulation: The gel comprises the compounds of the invention in PBS (phosphate buffered saline, see L. HUDSON and F. C. HAY (1980) Practical Immunology, Oxford, sec. edition) with 3% (w/v) hydroxylethylcellulose.

The control group receives a gel comprising 3% (w/v) hydroxylethylcellulose in PBS.

The mechanical properties of the cervix are measured by the method described above which allows the quantification of cervical extensibility and dilation of the uterine cervix under isometric conditions.

Figure 1A:
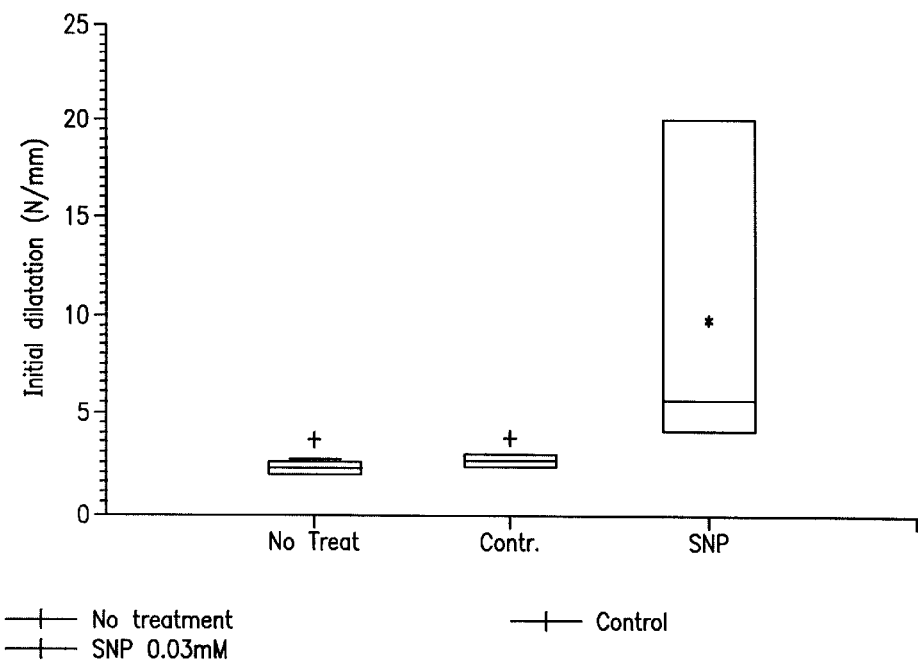
Figure 1B:
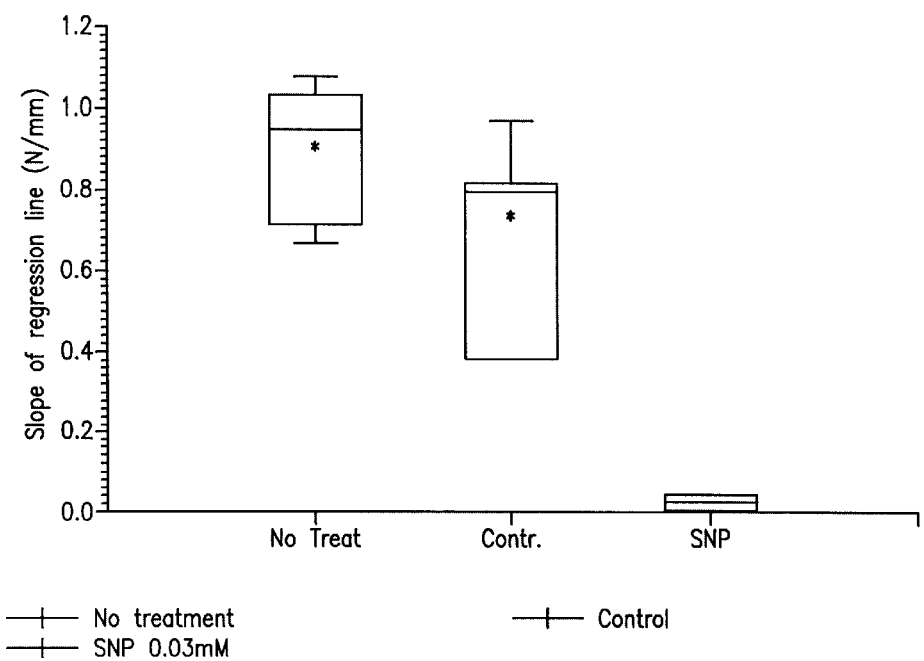

(d) Results:

The results of the Example 1 are shown in FIG. 1. The upper panel shows the slopes of the regression line which is the parameter of the extensibility of the cervix. The lower panel demonstrates the initial dilatation in mm of the cervix.

The results demonstrate that the NO donor sodium nitroprusside (SNP) after local administration in gel dramatically increases the cervical ripening in pregnant guinea pigs.

EXAMPLE 2

Effects of Sodium Nitroprusside (SNP) on the Morphology of the Cervix in Pregnant Guinea Pigs SNP (0.1 M) was administered intracervically in 0.2 ml PBS buffer containing 3% hydroxycellulose twice on days (d) 42–43 post coitum (p.c.), and the effects were assessed on day 44 p.c. by morphological evaluation. The control animals were treated with the vehicle. All cervices used for the morphological evaluation were obtained after in situ fixation by vascular perfusion. The perfusion procedure was performed on day 50 p.c. between 9–10 a.m. under anesthesia with 1,5 ml pentobarbital i.m. (60 mg/ml). A cannula was implanted into the abdominal aorta beneath the branching of renal arteries; animals were perfused with cacodylate buffer, pH 7,4 for 60–90 sec, followed by fixation with 2,5% glutaraldehyde in cacodylate buffer, pH 7.4, for 6–10 min at a pressure of 80–100 cm. $H_2O$. Cervices were excised and dissected free of adjacent tissues, then fixed at 4° C. in the same fixative. After buffer wash, the material was post-fixed for 2 h in cold cacodylate buffered 1% OsO4, dehydrated in graded series of ethanol and embedded in Araldite epoxy resin. Transverse semithin survey sections, 1–2 $\mu m$ in thickness, were cut from each of these specimens and were stained with 1% toluidine blue in sodium borate to be examined by light microscopy. This enabled to study the entire cervix, thereby providing an overview of the distribution of the various cell populations in the cervix. Thereafter, small specimens (1–2 $mm^3$) were trimmed off the transverse cervix block and ultrathin sections were prepared with glass or diamond knives on a Reichert OmU3 microtome and mounted on single slot Formvar-coated copper grids. They were stained with uranyl acetate and lead citrate and examined with a Zeiss EM-10 electron microscope at 60–80 kW.

An electron microscope study revealed a pronounced cervical ripening accompanied by the dissolution of collagen fibres, stromal edema, arterial dilatation, and the infiltration of macrophages, lymphocytes and granulocytes. Numerous mast cells were also present. The morphological effects of SNP were similar to those observed during normal cervical ripening at term, or after treatment with the antiprogestin onapristone or the cytokine IL-8.

EXAMPLE 3

Effects of L-NAME on the Uterine Cervix in Pregnant Guinea Pigs

Figure 2A:
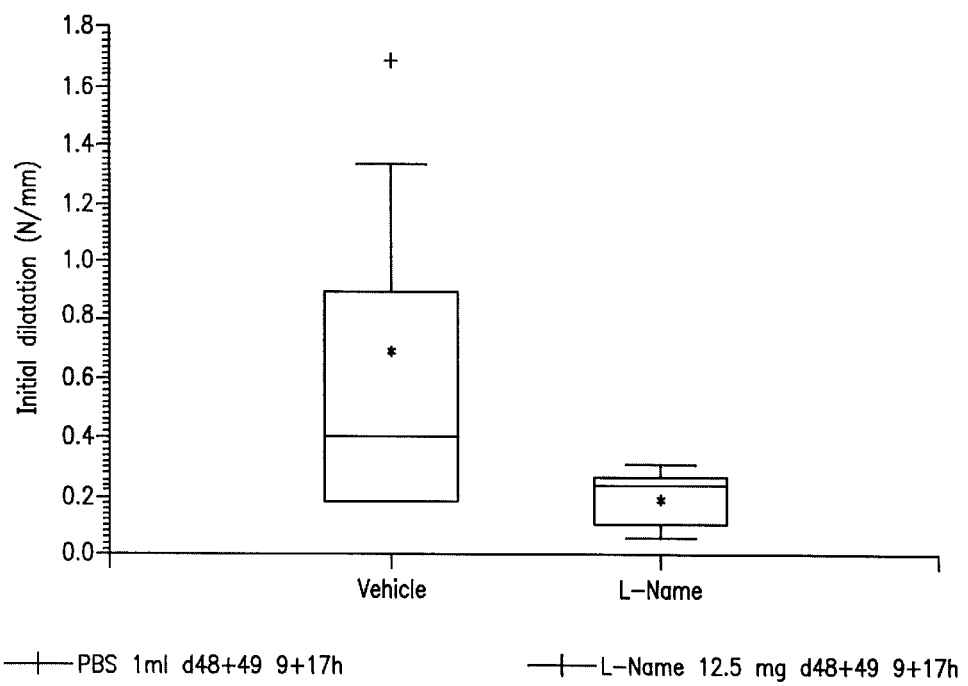
Figure 2B:
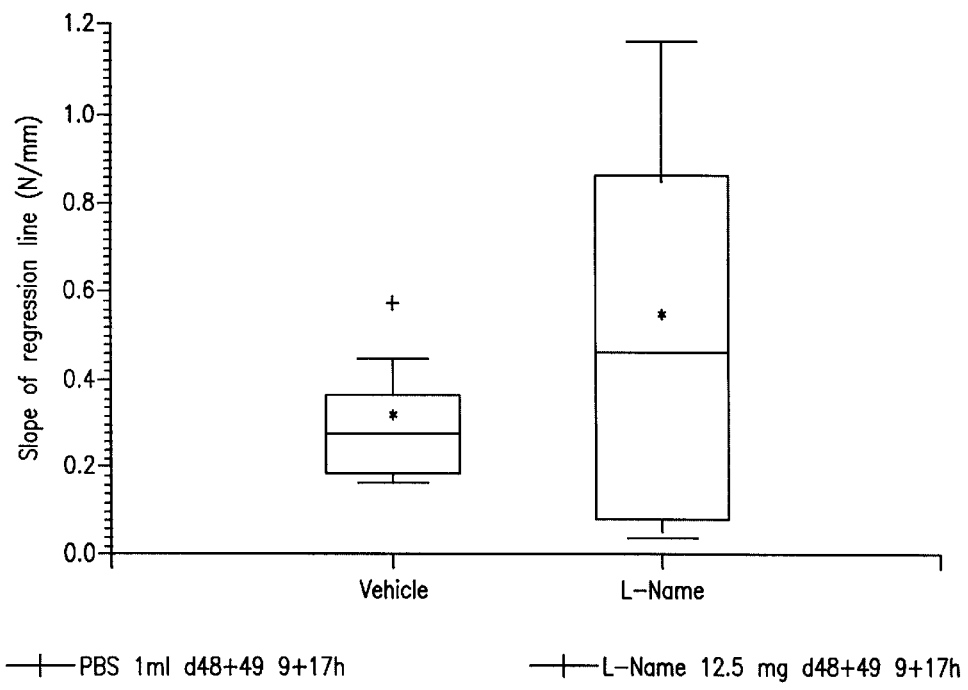
Figure 3:
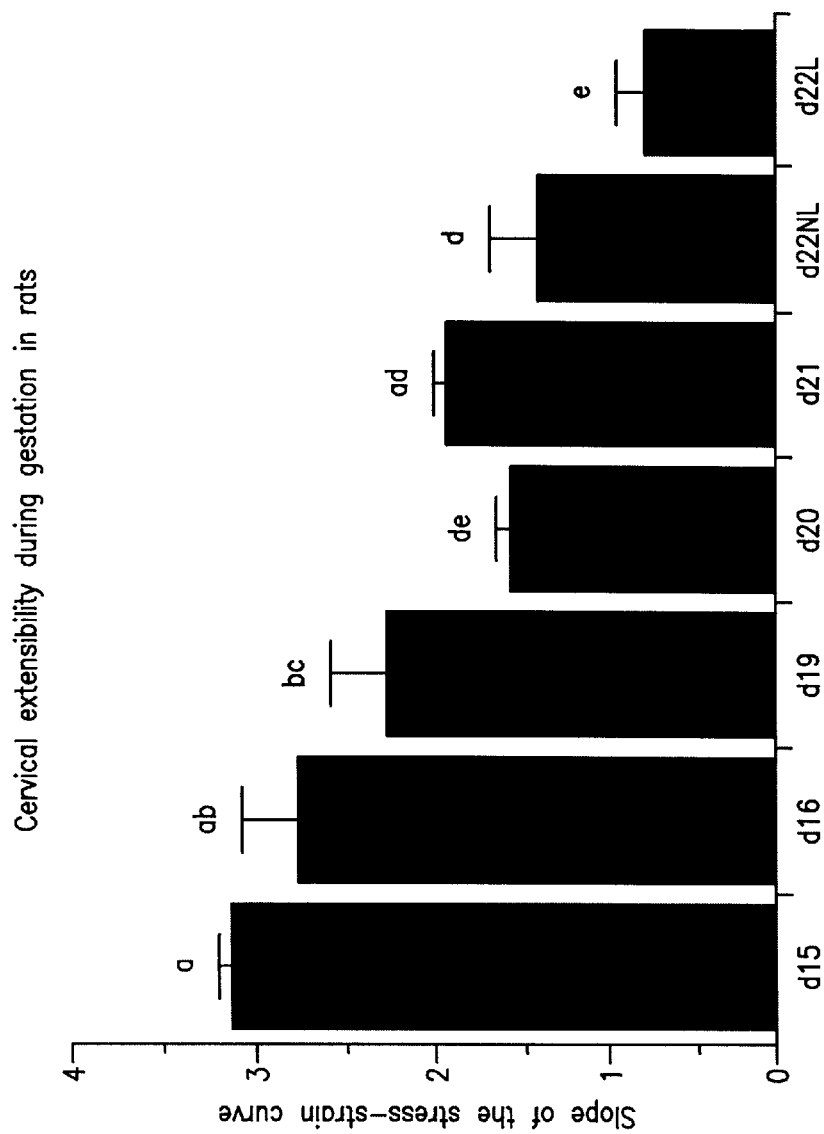
FIGS. 3 to 5 show extensibility of the cervix of rats after treatment with L-NAME (50 mg/rat) or without treatment.
Figure 4:
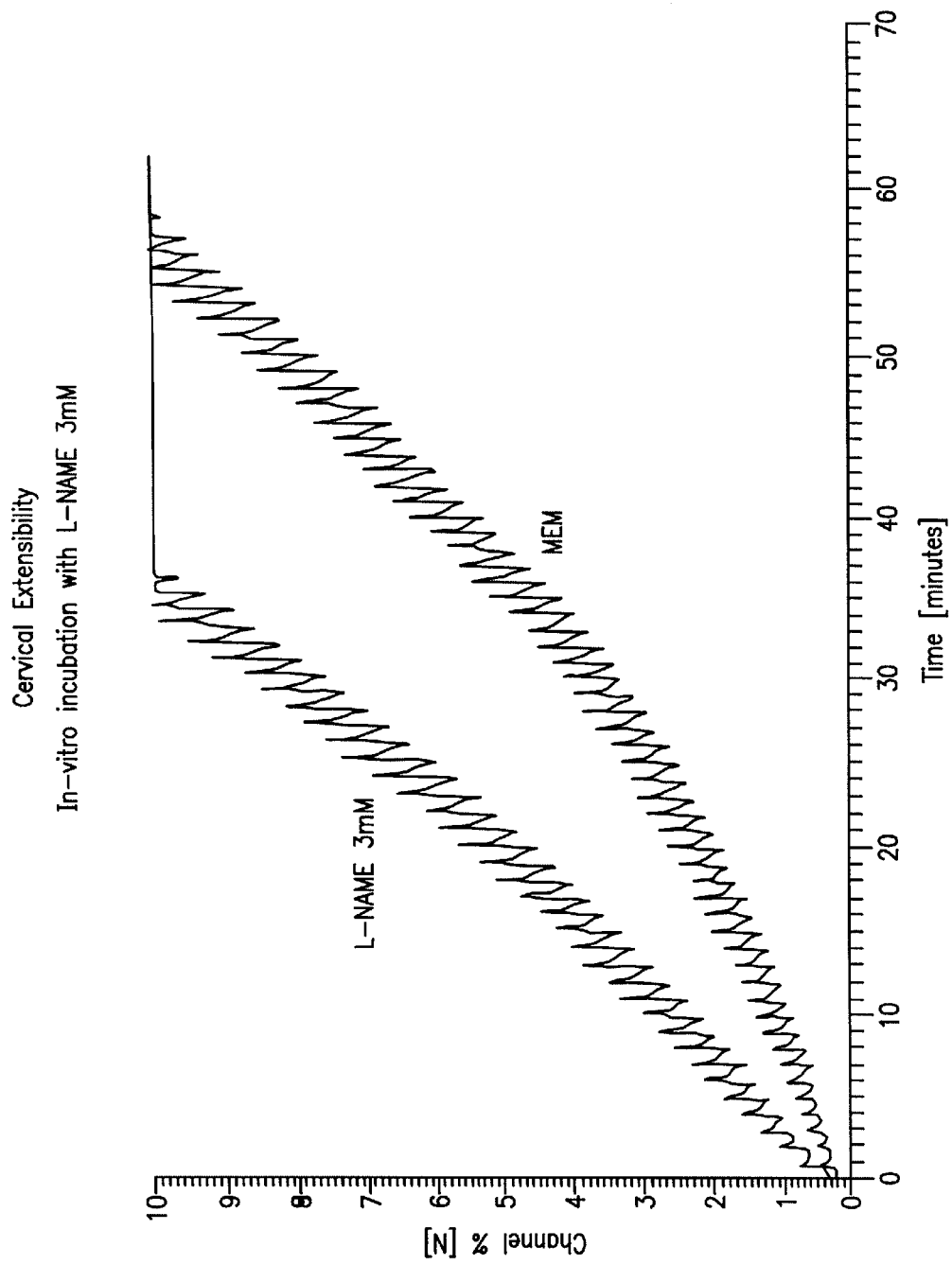
Figure 5:
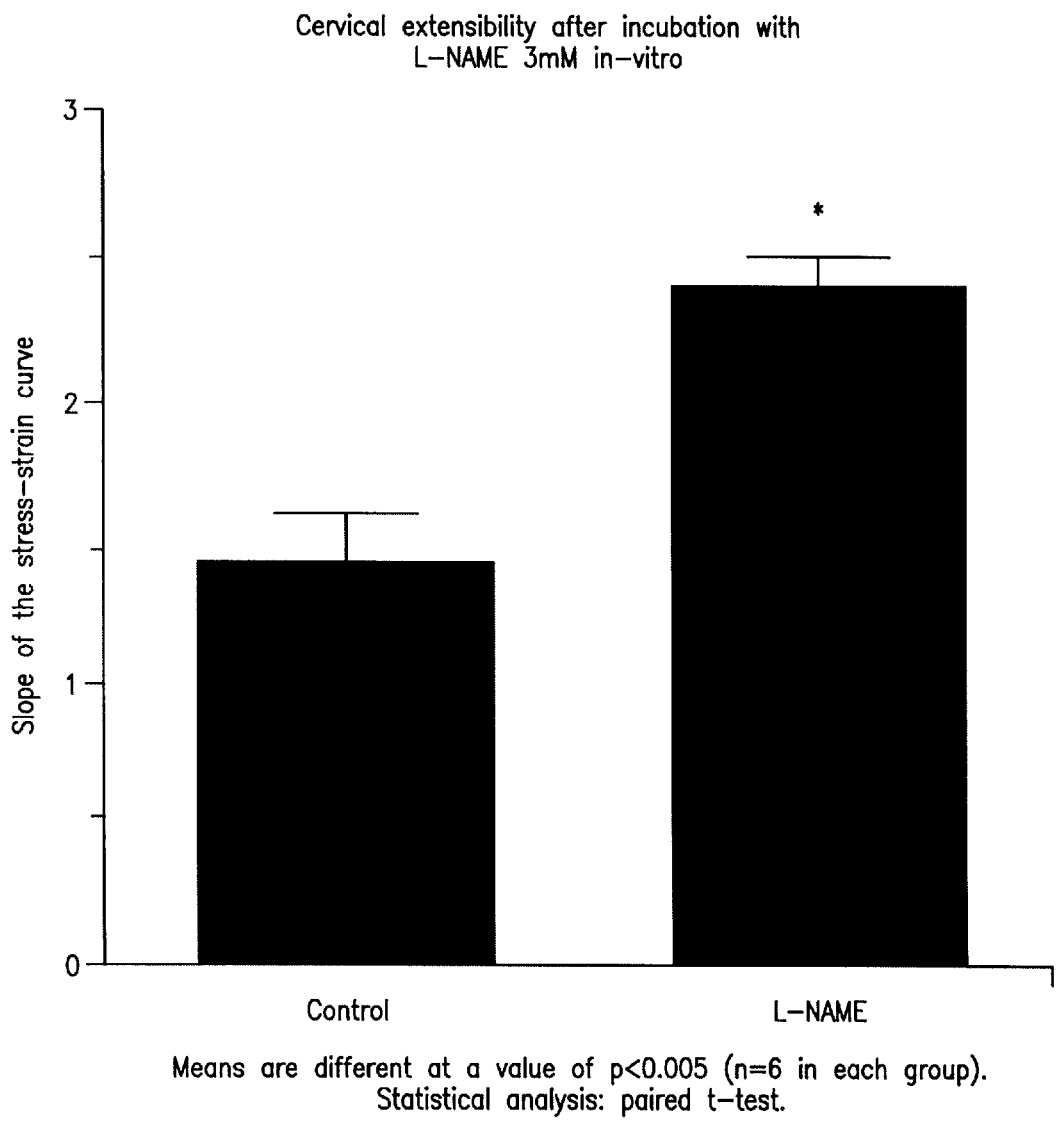

Pregnant guinea pigs were treated with L-NAME (12.5 mg/day/animal s.c.) on days 48 and 49 p.c. The cervical extensibility and dilatation were measured on day 50 p.c., i.e. two days after the start of tratment. The measurement was conducted as described in Example 1. The results of Example 3 are shown in FIG. 2. Both the initial dilatation and cervical extensibility (increase in slope) were decreased in comparison with the control group.

EXAMPLE 4

Effects of L-NAME on Parturition in Pregnant Guinea Pigs

Osmotic minipumps containing L-NAME (group 1:7 mg; group 2: 12,5 and group 3:25 mg/animal/day) were implanted subcutaneously on day 50 p.c. (term=day 67+2 p.c.). The control group was treated with the vehicle:

All animals (5/5) of group 3 and 3/5 of group 2 delivered prematurely (before day 65 p.c.) within 8 days of treatment.

This study shows that L-NAME induces preterm parturition in guinea pigs by the activation of uterine contractions. However, prolonged deliveries lasting several hours were observed in animals treated with L-NAME. This observation is an indirect indication of deficient cervical ripening which was demonstrated in a separate experiment performed on day 50 p.c by using extensibility measurement of the cervix (FIG. 2).

EXAMPLE 5

Effects of L-NAME on Parturition in Rats

Figure 6B:
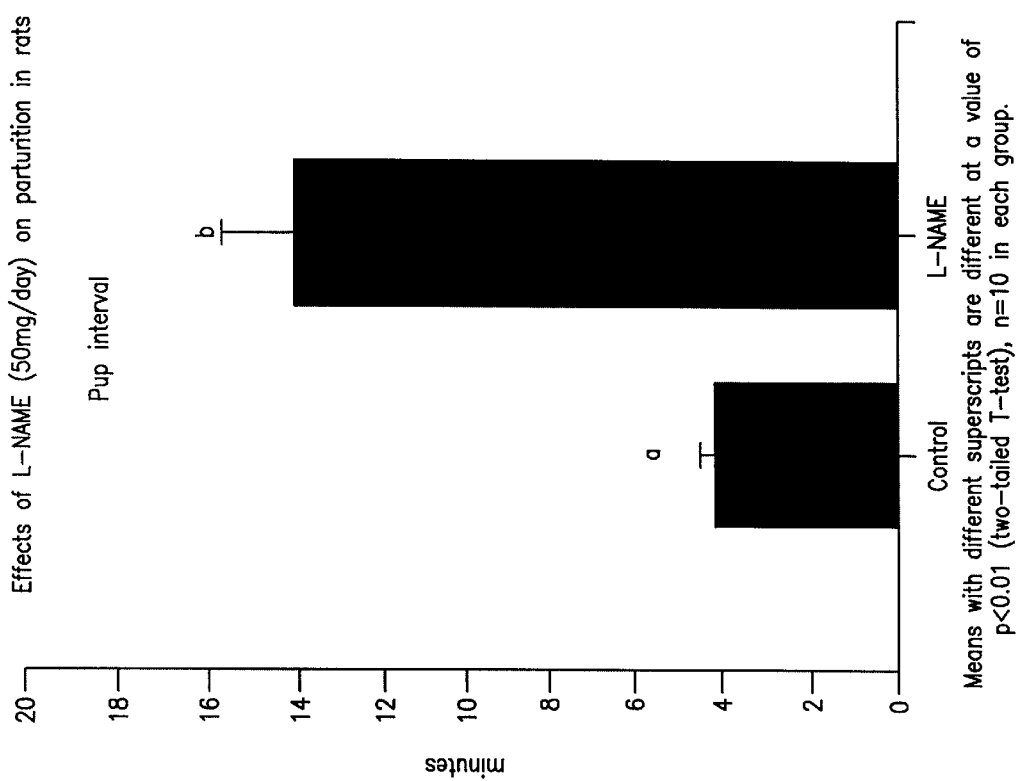
FIGS. 6 (A and B) shows increase in duration of delivery (FIG. 6A) and pup interval (FIG. 6B) (time between birth of pups during L-NAME treatment.
Figure 6A:
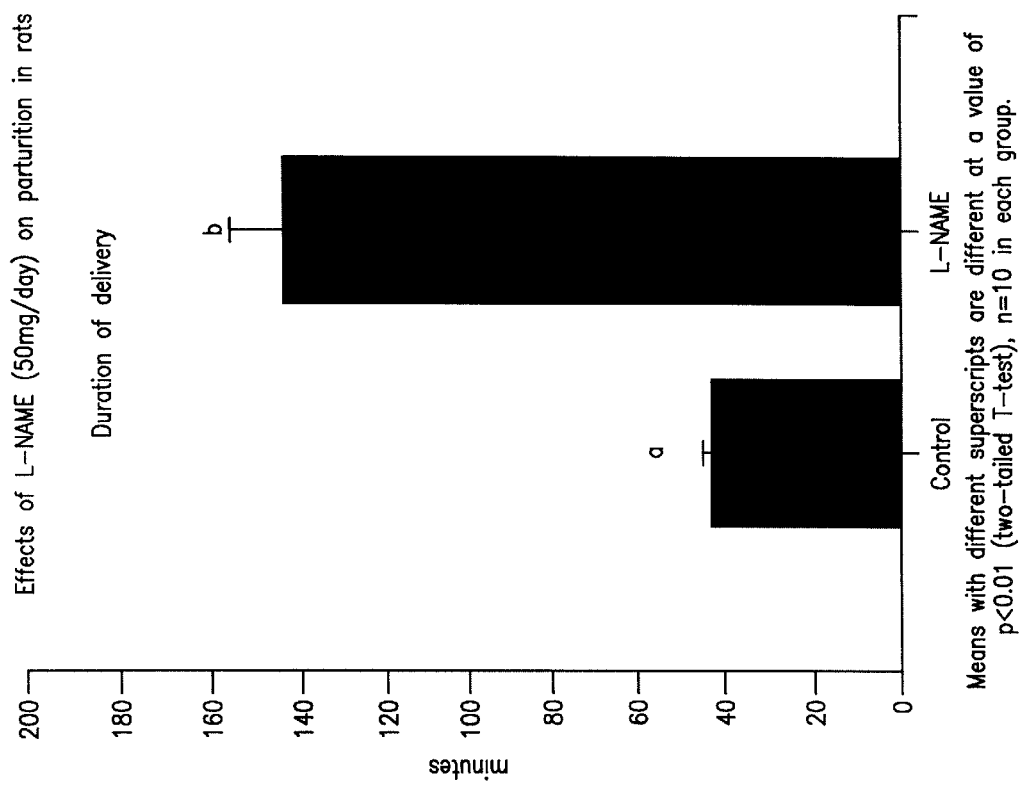

FIG. 6 which is based on a similar experiment as that described in Example 4 shows that during L-NAME treatment (50 mg/day) of pregnant rats the duration of delivery and the pup intervall, that is the time between the birth of the single pups, is markedly increased. This clearly shows that nitric oxide inhibitors prevent cervical ripening in rats.

EXAMPLE 6

Nitric Oxide Production in the Rat During Normal Cervical Dilatation. After Progesterone. Antiprogestine and LPS Treatment (a) Method The nitric oxide generating activity measured in vitro as a total nitrite accumulation in the cervical and uterine tissues was estimated using a method described in: *Yallampalli C, Garfield RE, Dyam-Smith M* (1993): *Nitric oxide inhibits uterine contractility during pregnancy but not during delivery, Endocrinology* 133: 1899–1902. Briefly, small pieces of cervical or uterine tissues obtained from delivering rats (day 22–23 of pregnancy), onapristone-treated (10 mg on day 18 p.c., s.c.) and from vehicle-treated rats on days 18–21 p.c. (controls) were incubated in minimum essential medium (MEM) with L-arginine with or without L-NAME for 24 h at 37° C. The medium was assayed for total nitrites using the Griess reagent.

(b) Results

Nitrite production in the uterine (myometrial) tissue: the production dramatically decreases in the uterine samples obtained from delivering animals in comparison with day 18 of pregnancy (Yallampalli et al., loc. cit).

Figure 7:
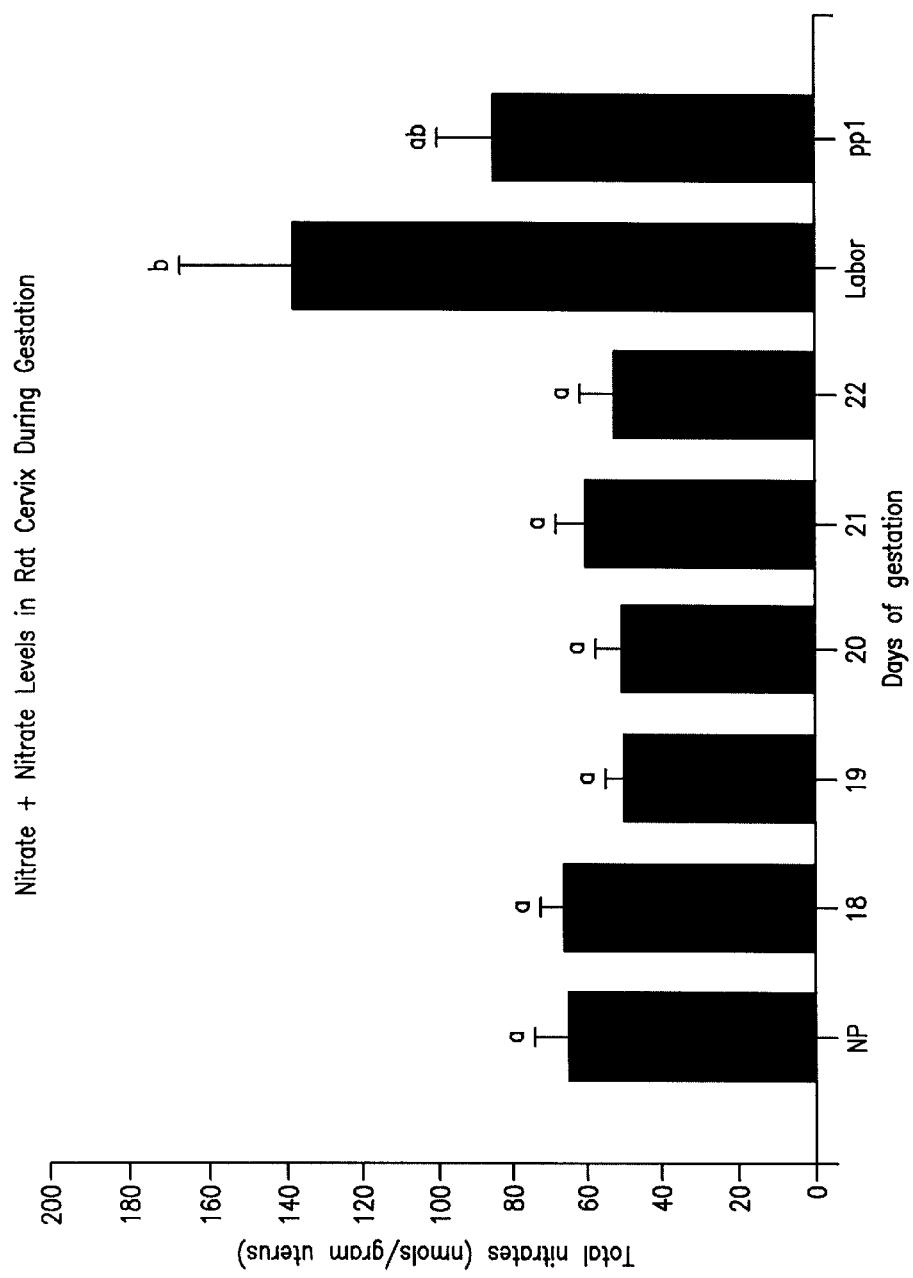
FIGS. 7 to 9 show NO production during normal cervical dilatation (↑), after progesterone (↓) antiprogestine (↑,), and LPS (↑,).

Nitrite production in the cervical tissue (FIG. 7): there is a significant increase in NO production in the cervix obtained from delivering animals in comparison with pregnant rats on days 18–22 p.c.

Figure 8:
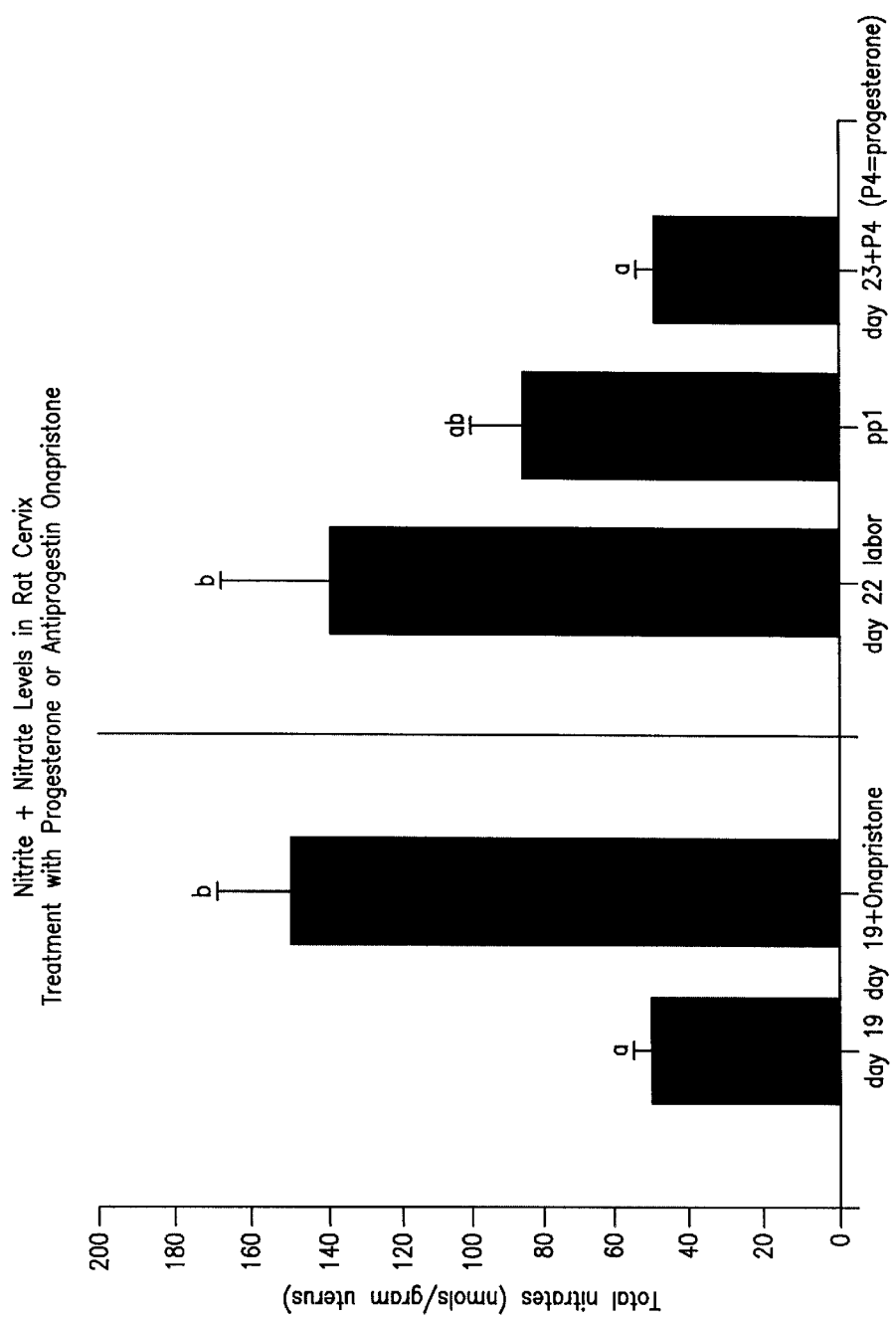
Figure 9:
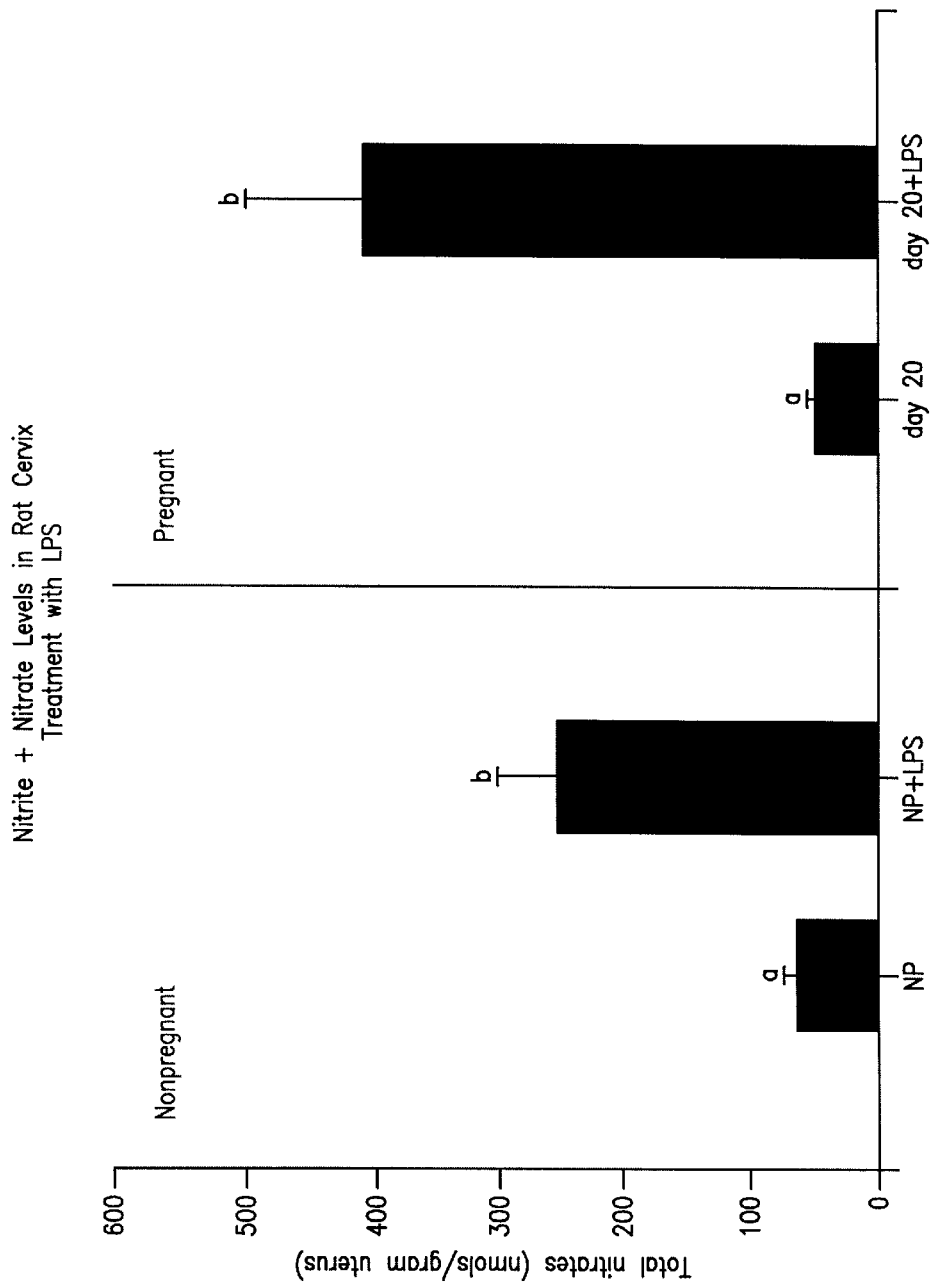

Effect of onapristone on the NO production in the uterine cervix (FIG. 8): there is a significant increase in cervical NO production in comparison with the control group on day 19 p.c. to levels seen in spontaneously delivering animals.

EXAMPLE 7

Pre-induction of Cervical Ripening with a Nitric Oxide Donor

To a pregnant woman (ca. 30 years, 50–80 kg) at 38th week of gestation who was classified to labor induction because of preeclampsia, administer sodium nitroprusside at the concentration of 0.01–0.1 mM in gel intracervically twice-a-day in order to achieve cervical ripening. Labor induction will be performed on the next day using oxytocin i.v. infusion.

EXAMPLE 8

Treatment of Cervical Insufficiency with a Local Application of L-NAME

To a pregnant woman (ca. 30 years, 50–80 kg) at the 26 week of pregnancy displaying the signs of cervical insufficiency (cervical dilatation, softening of the cervix) administer L-NAME in gel intracervically or intravaginally at the concentration of 0.1–50 mg/ml in two to three doses a day until the amelioration of symptoms of cervical insufficiency.

What is claimed is:

1. A method of inducing cervical dilatation and/or extensibility, comprising administering, intracervically, intravaginally, or to the surface of the cervix, to a patient in need of such treatment an amount of at least one nitric oxide donor and/or substrate effective to induce cervical ripening.

2. A method of claim 1, wherein cervical ripening of a non-pregnant female or pregnant female is induced to assist in surgical or diagnostic procedure.

3. A method of claim 1, wherein cervical ripening is induced for a female to be treated by in vitro fertilization.

4. A method of claim 1, comprising administering at least one of L-arginine, sodium nitroprusside, nitroglycerin, glyceryl trinitrate, SIN-1, isosorbid mononitrate, and isosorbid dinitrate as a nitric oxide substrate and/or donor.

5. A method of claim 1, wherein said inducing of cervical dilation and/or extensibility is achieved in a patient in need of induction of labor.

6. A method of claim 1, wherein said inducing of cervical dilation and/or extensibility is achieved in a patient in need of induction of abortion.

7. A method of inhibiting cervical dilation and/or extensibility, comprising administering, intracervically, intravaginally, or to the surface of the cervix, to a patient in need of such treatment, an amount of at least one nitric oxide inhibitor effective to inhibit said dilation and/or extensibility.

8. A method of claim 7, wherein said inhibiting of cervical dilation and/or extensibility is achieved in a patient suffering from cervical insufficiency.

9. A method of claim 7, wherein said inhibiting of cervical dilation and/or extensibility is achieved in a patient suffering from threatening preterm labor.

10. A method of claim 7, comprising administering at least one of NG-nitro-L-arginine methyl ester (L-NAME), NG-monoethyl-L-arginine (l-MMA), N-iminoethyl-L-arnithine (L-NIO), L-monomethyl-L-arginine (L-NNMA), L-NG-methyl-arginine (L-NMA), Nw-nitro-L-arginine (L-NA) and Aminoguanidine as a nitric oxide inhibitor.

11. A method of claim 7, wherein said inhibiting of cervical dilation and/or extensibility is achieved in a patient suffering from preterm labor.

12. A method of inducing labor, comprising administering, intracervically, intravaginally, or to the surface of the cervix, to a patient in need of such treatment, an amount of at least one nitric oxide donor and/or substrate effective to promote labor.

13. A method of claim 12, comprising further administering at least one of an antiprogestin, a prostaglandin and/or a cytokine.

14. A method of claim 13, comprising administering at least one of onapristone (11β-[4-(Dimethylamino)phenyl]-17α-hydroxy-17β-(3-hydroxypropyl)-13α-estra-4,9-diene-3-one), RU486(11β-[4-(Dimethylamino)phenyl]-17β-hydroxy-17α-(1-propinyl)estra-4,9-diene-3-one), (Z)-11β-[4-(Dimethylamino)phenyl]-17β-hydroxy-17α-(3-hydroxy-1-propinyl)estra-4-ene-3-one (EP-A 0 404 283), 11β-(4-Acetylphenyl)-17β-hydroxy-17α-(1-propinyl)estra-4,9-diene-3-one (EP-A 0 190 759), 4',5'-Dihydro-11β-[4-(dimethylamino)phenyl]-6β-methylspiro[estra-4,9-diene-17β-,2'(3'H)-furan]-3-one, 4',5'-Dihydro-11β-[4-(dimethylamino)phenyl]-7β-methylspiro[estra-4,9-diene-17β,2'(3'H)-furan]-3-one 11β-(4-Acetylphenyl)-19,24-dinor-17,23-epoxy-17α-chola-4,9,20-triene-3-one, (E)-11β-

[4-[[(Acetyloxy)imino]methyl]penyl]-17β-methoxy-17α-(methoxymethyl)estra-4,9-diene-3-one (E)-11β-[4-[[[(Ethoxycarbonyl)oxy]imino]methyl]phenyl]-17β-methoxy-17α-(methoxymethyl)-estra-4,9-diene-3-one as an antiprogestin.

15. A method of claim 13, comprising administering PGE$_2$, or Gemeprost as a prostaglandin.

16. A method of claim 13, comprising administering interleukin-8, or interleukin-1β as a cytokine.

17. A method of claim 12, wherein labor is induced at term.

18. A method of claim 12, wherein labor is induced in connection with a pathological pregnancy.

19. A method of claim 12, wherein labor is induced in connection with intrauterine fetal death.

20. A method of claim 12, wherein said inducing of labor is achieved in a patient in need of abortion.

21. A method of claim 12, wherein said labor is preterm labor.

22. A method of claim 12, wherein said inducing of labor is achieved in a patient in need of management of prolonged labor.

23. A method of promoting labor, comprising administering, intracervically, intravaginally, or to the surface of the cervix, to a patient in need of such treatment, an amount of at least one nitric oxide donor and/or substrate effective to induce labor.

24. A method of inhibiting preterm labor, comprising administering, intracervically, intravaginally, or to the surface of the cervix, to a patient in need of such treatment, an amount of at least one nitric oxide inhibitor effective to inhibit preterm labor.

25. A method of claim 24, comprising further administering at least one of a progestin and/or a cyclooxygenase inhibitor (COX-1-and COX-2-inhibitors).

26. A method of claim 25, comprising administering progesterone as a progestin.

27. A method of claim 25, comprising administering aspirin as a cyclooxygenase inhibitor.

28. A method of claim 25, comprising administering flusolide as a COX-2 inhibitor.

29. A method of claim 24, comprising administering at least one of NG-nitro-L-arginine methyl ester (L-NAME), NG-monoethyl-L-arginine (l-MMA), N-iminoethyl-L-arnithine (L-NIO), L-monomethyl-L-arginine (L-NNMA), L-NG-methylarginine (L-NMA), Nw-nitro-L-arginine (L-NA) and Aminoguanidine as a nitric oxide inhibitor.

30. A method of inducing abortion, comprising administering, intracervically, intravaginally, or to the surface of the cervix, to a patient in need of such treatment, an amount of at least one nitric oxide donor and/or substrate effective to induce abortion.

31. A method of treating cervical insufficiency, comprising administering, intracervically, intravaginally, or to the surface of the cervix, to a patient in need of such treatment, an amount of at least one nitric oxide inhibitor effective to treat cervical insufficiency.

* * * * *